United States Patent [19]

Miyazawa et al.

[11] Patent Number: 4,900,472
[45] Date of Patent: Feb. 13, 1990

[54] 2,5-DIPHENYL PYRIMIDINE COMPOUNDS AND LIQUID CRYSTAL COMPOSITIONS

[75] Inventors: Kazutoshi Miyazawa, Yokohama; Makoto Ushioda, Kawasaki; Hiromichi Inoue, Yokohama; Shinichi Saito, Yokohama; Kouji Ohno, Yokohama, all of Japan

[73] Assignee: Chisso Corporation, Osaka, Japan

[21] Appl. No.: 260,519

[22] Filed: Oct. 20, 1988

[30] Foreign Application Priority Data

Oct. 20, 1987 [JP] Japan ................................ 62-262819
Oct. 20, 1987 [JP] Japan ................................ 62-262821

[51] Int. Cl.$^4$ ..................... G02F 1/13; C09K 19/34; C07D 239/02
[52] U.S. Cl. ..................... 252/299.61; 252/299.01; 252/299.5; 350/350 R; 350/350 S; 544/335
[58] Field of Search ............ 252/299.61, 299.01, 252/299.5; 350/350 R, 350 S; 544/335

[56] References Cited

U.S. PATENT DOCUMENTS

| | | | |
|---|---|---|---|
| 4,725,688 | 2/1988 | Taguchi et al. | 252/299.61 |
| 4,744,918 | 5/1988 | Heppke et al. | 252/299.61 |
| 4,764,636 | 8/1988 | Sasaki et al. | 252/299.61 |
| 4,765,924 | 8/1988 | Inoue et al. | 252/299.61 |
| 4,775,223 | 10/1988 | Yoshinaga et al. | 252/299.61 |
| 4,818,430 | 4/1989 | Saito et al. | 252/299.61 |
| 4,820,839 | 4/1989 | Krause et al. | 252/299.61 |
| 4,834,904 | 5/1989 | Krause et al. | 252/299.61 |

FOREIGN PATENT DOCUMENTS

| | | | |
|---|---|---|---|
| 206228 | 12/1986 | European Pat. Off. | 252/299.61 |
| 255219 | 2/1988 | European Pat. Off. | 252/299.61 |
| 3515373 | 11/1986 | Fed. Rep. of Germany | 252/299.61 |
| 61-215374 | 9/1986 | Japan | 252/299.61 |
| 63-51377 | 3/1988 | Japan | 252/299.61 |
| 63-172788 | 7/1988 | Japan | 252/299.61 |
| 63-182395 | 7/1988 | Japan | 252/299.61 |
| 63-253075 | 10/1988 | Japan | 252/299.61 |
| 86/06401 | 11/1986 | World Int. Prop. O. | 252/299.61 |
| 87/05018 | 8/1987 | World Int. Prop. O. | 252/299.61 |

OTHER PUBLICATIONS

Saito, S. et al., 1988 International Display Research Conf., IEEE, pp. 107-110 (Oct. 4-6, 1988).
Demus, D. et al., Flussige Kristalle in Tabellen, VEB Deutscher Verlag fur Grundstoffindustrie, Leipzig, pp. 261-263 (1974).

*Primary Examiner*—Teddy S. Gron
*Attorney, Agent, or Firm*—Wenderoth, Lind & Ponack

[57] ABSTRACT

The present invention provides optically active compounds represented by the following general formula:

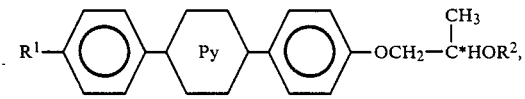

liquid crystal compositions containing the compounds, and electro optical elements using the above compositions.

The compounds of the present invention are optically active compounds having characteristics suited for a ferroelectric liquid crystal composition, especially having enough spontaneous polarization to realize quick response.

11 Claims, No Drawings

2,5-DIPHENYL PYRIMIDINE COMPOUNDS AND LIQUID CRYSTAL COMPOSITIONS

BACKGROUND OF THE INVENTION

The present invention relates to new organic compounds and liquid crystal compositions containing the compounds, and more particularly, the present invention relates to optically active compounds having an optically active group, liquid crystal compositions containing the compounds and electro optical elements using the compositions.

Liquid crystal display elements are widely used as various display elements, such was watches, electronic calculators, television sets, computer ends, etc., because these elements have excellent characteristics, such as operatively at low voltage, minimized consumption of electric power, obtainability of thin display elements and so on.

At present, display elements of a twisted nematic (TN) type are widely used as liquid crystal display elements. However, the response of the display element is slower than that of a display element of light emitting type such as an electroluminescence display, a plasma display, and the like. Although improvement of the response time of the liquid crystal display has been tried in many ways, it shows no sign of marked improvement.

However, a new display method using a ferroelectric liquid crystal that has been studied has hope for the improvement of the response time. (Clark et al., Appl. Phys. Lett., 36, 899(1980)). This display method utilizes a ferroelectric chiral smectic C phase (abbreviated as $S_c^*$ phase hereinafter) or other smectic phase such as a chiral smectic F, G, H or I phase, and the like. This method has a quick response time less than 1/100 to 1/1000 of that of the TN display method and a memory effect of bistability. It is expected to have wide application of a large sized television set of dynamic picture display, a high-speed light shutter, and the like.

However, in spite of these excellent characteristics, already-known compounds do not show a very quick response The reason is that a compound having a high value of spontaneous polarization in the ferroelectric liquid crystal phase is unknown. The spontaneous polarization value is proportional to the response rate. It is known that the high value of spontaneous polarization is important to obtain the quick response, but compounds having the high value of spontaneous polarization were not found.

An object of the present invention is to provide optically active compounds having characteristics suited for the display method which is still being researched, especially having enough spontaneous polarization to realize a quick response.

SUMMARY OF THE INVENTION

The present invention resides in an optically active compound represented by the following general formula:

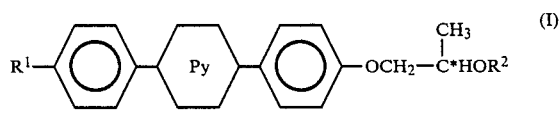

wherein $R^1$ indicates an alkyl or alkoxy group having 1-20 carbon atoms, $R^2$ indicates an alkyl, acyl or alkoxyacyl group having 1-20 carbon atoms,

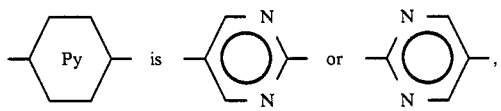

and * indicates an asymmetric carbon atom. The present invention also resides in a liquid crystal composition containing at least one of the above compounds.

The phase transition temperatures of the representative compounds (I) of the present invention are shown in Table 1.

TABLE 1

| Compound No. | $R^1$ | Py | $R^2$ | Absolute Configuration | C | Phase Transition Temperature(°C.) $S_c^*$   $S_A$ | | I | Note |
|---|---|---|---|---|---|---|---|---|---|
| 1 | n-C4H9 | (pyrimidine N-N) | —C6H13 | R | • | 83.0 —• | 136.0 | • | Example 3 |
| 2 | n-C4H9 | (pyrimidine N-N) | —CO—C4H9 | S | • | 121.5 —• | 136.0 | • | Example 1 |
| 3 | n-C4H9 | (pyrimidine N-N) | —CO—C*HOC4H9 (CH3) | S,S | • | 128.7 —(• | 116.0) | • | Example 2 |
| 4 | n-C9H19 | (pyrimidine N-N) | —C6H13 | R | • | 81.4 • 109.0 | — | • | |

TABLE 1-continued

| Compound No. | R¹ | -Py- | R² | Absolute Configuration | C | Phase Transition Temperature(°C.) $S_C^*$ | $S_A$ | I | Note |
|---|---|---|---|---|---|---|---|---|---|
| 5 | n-$C_9H_{19}$ | pyrimidine | —CO—$C_4H_9$ | S | • | 123.2 | — | — | • |
| 6 | n-$C_9H_{19}$ | pyrimidine | —CO—C*H($CH_3$)$C_2H_5$ | S,S | • | 109.5 | — | — | • |
| 7 | n-$C_9H_{19}$ | pyrimidine |  | S,S | • | 121.1 | — | — | • |
| 8 | n-$C_9H_{19}$ | pyrimidine | —CO—C*H($CH_3$)O$C_4H_9$ | S,S | • | 98.0 | — | — | • Example 4 |

The compounds of the present invention do not necessarily have the ferroelectric liquid crystal phase, but all of them act to substantially increase spontaneous polarization as a component in a ferroelectric liquid crystal composition, so that the compounds can accelerate the response rate. As shown in the examples described hereinafter, when several or tens percents by weight of the compound of the present invention is added to a liquid crystal composition having a non-chiral smectic C phase which does not show spontaneous polarization, the composition induces substantially high value of spontaneous polarization. As a result, a composition which shows a short response time of 40 μsec at 15° C. is obtained as described in Example 5.

Considering the fact that the response time of known compounds described in Japanese patent application Nos. 62-132800/1987 and 62-103977/1987 are 48 μsec and 125 μsec at the same conditions, respectively, and that the responses are regarded as the best quick responses, it is found that the composition has a surprising characteristic.

As the compounds of the present invention have optically active carbon atoms, they can induce twisted structure by adding them to nematic liquid crystals. As the nematic liquid crystals having the twisted structure, namely chiral nematic liquid crystals, do not produce so-called reverse twist domain (stripe pattern) of the TN type display element, the compounds of the present invention can be used as an inhibitor of the reverse domain production.

When 1 percent by weight of the compound of the present invention is added to a nematic liquid crystal composition ZLI-1132 made by Merck Company, the determined pitch of the chiral nematic liquid crystal composition obtained by the addition of the compounds of the present invention, as shown in Example 6, is short, i.e. 10.9μm at 25° C. It is found that necessary pitch length is obtained by adding a small quantity of compounds of the present invention to the chiral nematic crystal compositions, and these compounds act as a useful pitch controlling agent.

Furthermore, the compounds have good temperature characteristics and the temperature characteristic $\sigma_p$ represented by the following formula:

$$\sigma_p = \frac{2(p(t_1) - p(t_2))}{p(t_1) + p(t_2)} \times \frac{100}{t_1 - t_2}$$

wherein p(t) is a pitch at t° C. and t indicates a temperature, is −0.017 and it is very flat at $t_1=20°$ C. and $t_2=70°$ C.

This is a surprising characteristics because, for example, the $\sigma_p$ of a well-known pitch controlling agent, namely S-4-(2-methylbutyl)-4'-cyanobiphenyl, in chiral nematic crystal compositions is 0.584 at the same conditions.

The production method of the compounds (I) of the present invention is described hereinafter.

An example of a method for preparing the compound (Ia) among the compounds (I) of the present invention, wherein

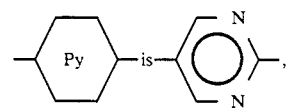

preferably includes the following process.

(1)

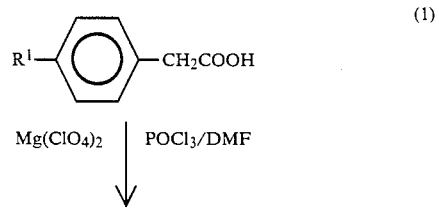

-continued

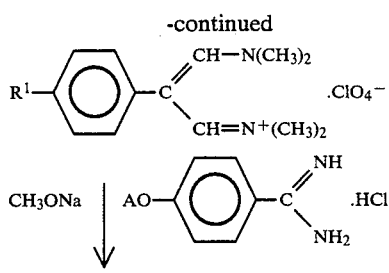

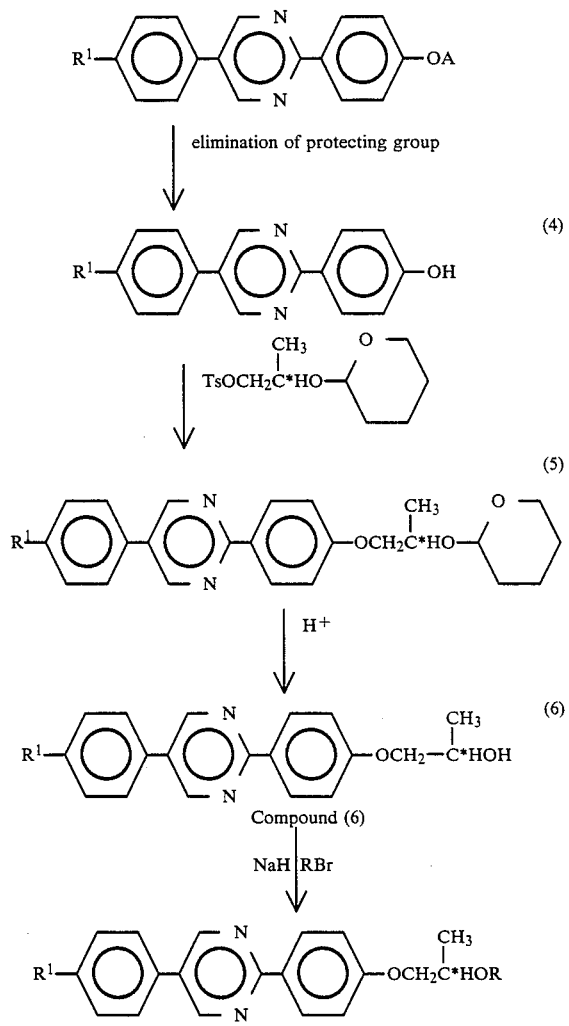

wherein R² indicates an alkyl group in formula (Ia).

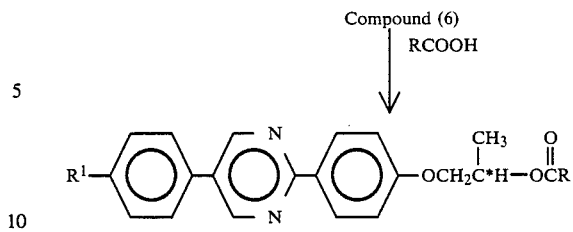

wherein R² indicates an acyl group in formula (Ia).

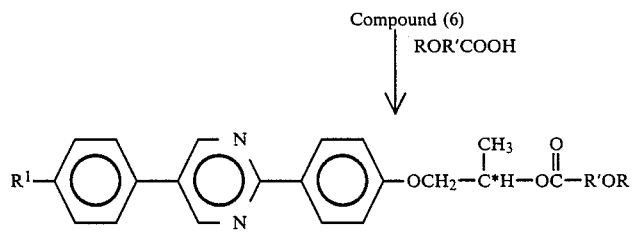

wherein R² indicates a alkoxyacyl group in formula (Ia).

In the above formulas, R' indicates a hydrocarbon of two valences and A indicates a protecting group such as methyl, benzyl and the like.

Compound (2) is obtained by reacting p-alkylphenyl acetic acid or p-alkoxyphenyl acetic acid (1) with phosphorous oxychloride, dimethylformamide and then a perchlorate. Compound (3) is obtained by reacting compound (2) with p-substituted benzamidine hydrochloride under basic conditions. After compound (4) is obtained by eliminating a protecting group of compound (3), compound (5) is obtained by reacting compound (4) with 2-tetrahydropyranyloxy-1-(p-toluenesulfonyloxy)propane which is described in Japanese patent application 62-132800/1986. Then, compound (6) is obtained by eliminating a protecting group of compound (5) under acidic conditions. Compounds of formula (Ia) wherein R² indicates an alkyl group are obtained by reacting compounds (6) with several kinds of alkyl halides under basic conditions, and compounds of formula (Ia) wherein R² indicates an acyl group and an alkoxyacyl group are obtained by reacting compound (6) with several kinds of fatty acids and alkoxy alkanoic acids, respectively.

Further, a compound (Ib) among the compounds (I) of the present invention, wherein

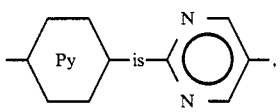

preferably is produced by the following process.

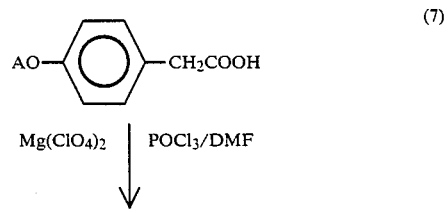

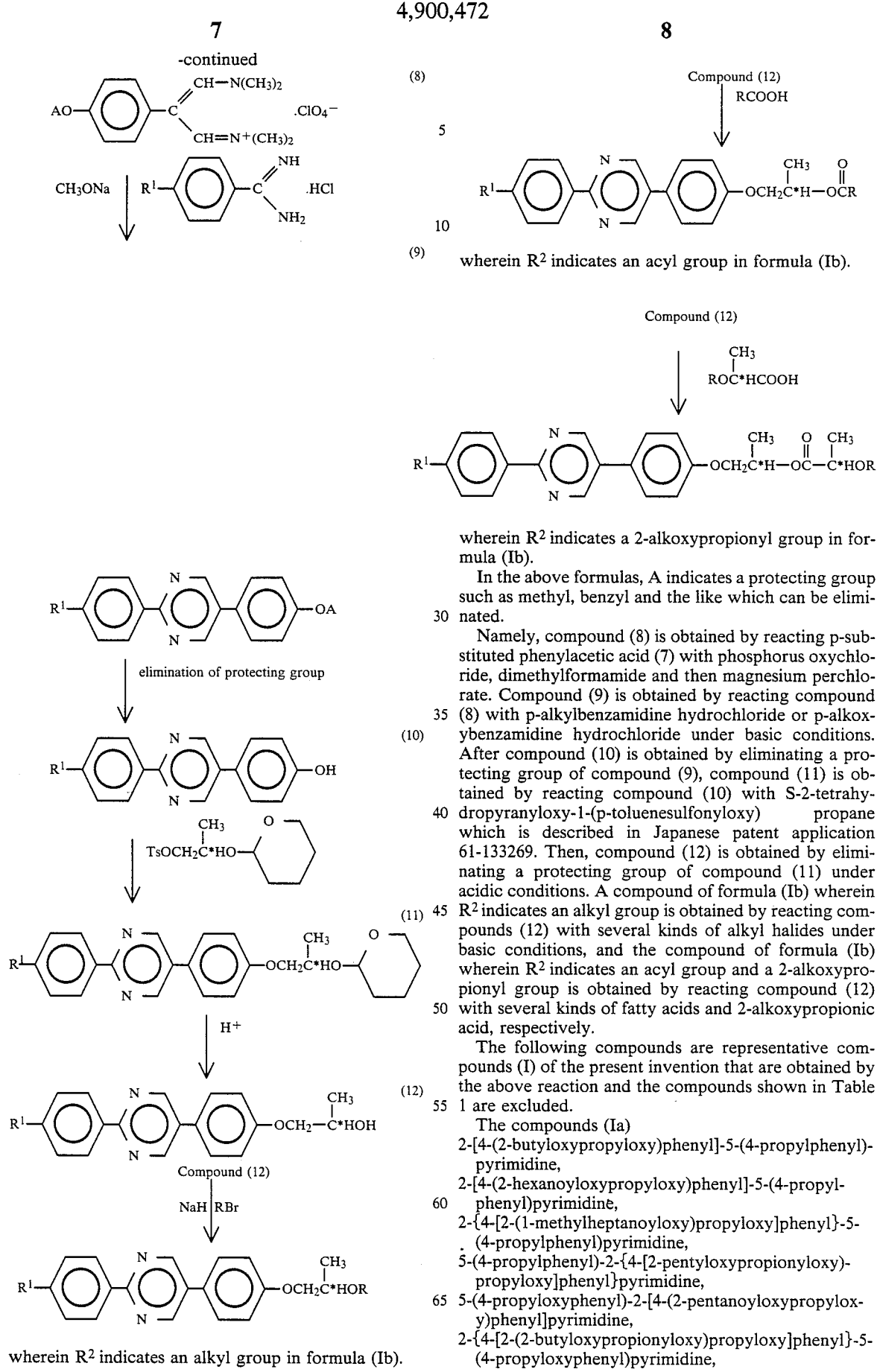

wherein $R^2$ indicates an acyl group in formula (Ib).

wherein $R^2$ indicates a 2-alkoxypropionyl group in formula (Ib).

In the above formulas, A indicates a protecting group such as methyl, benzyl and the like which can be eliminated.

Namely, compound (8) is obtained by reacting p-substituted phenylacetic acid (7) with phosphorus oxychloride, dimethylformamide and then magnesium perchlorate. Compound (9) is obtained by reacting compound (8) with p-alkylbenzamidine hydrochloride or p-alkoxybenzamidine hydrochloride under basic conditions. After compound (10) is obtained by eliminating a protecting group of compound (9), compound (11) is obtained by reacting compound (10) with S-2-tetrahydropyranyloxy-1-(p-toluenesulfonyloxy) propane which is described in Japanese patent application 61-133269. Then, compound (12) is obtained by eliminating a protecting group of compound (11) under acidic conditions. A compound of formula (Ib) wherein $R^2$ indicates an alkyl group is obtained by reacting compounds (12) with several kinds of alkyl halides under basic conditions, and the compound of formula (Ib) wherein $R^2$ indicates an acyl group and a 2-alkoxypropionyl group is obtained by reacting compound (12) with several kinds of fatty acids and 2-alkoxypropionic acid, respectively.

The following compounds are representative compounds (I) of the present invention that are obtained by the above reaction and the compounds shown in Table 1 are excluded.

The compounds (Ia)
2-[4-(2-butyloxypropyloxy)phenyl]-5-(4-propylphenyl)-pyrimidine,
2-[4-(2-hexanoyloxypropyloxy)phenyl]-5-(4-propylphenyl)pyrimidine,
2-{4-[2-(1-methylheptanoyloxy)propyloxy]phenyl}-5-(4-propylphenyl)pyrimidine,
5-(4-propylphenyl)-2-{4-[2-pentyloxypropionyloxy)propyloxy]phenyl}pyrimidine,
5-(4-propyloxyphenyl)-2-[4-(2-pentanoyloxypropyloxy)phenyl]pyrimidine,
2-{4-[2-(2-butyloxypropionyloxy)propyloxy]phenyl}-5-(4-propyloxyphenyl)pyrimidine, 5-(4-butylphenyl)-2-[4-(2-butyryloxypropyloxy)-phenyl]pyrimidine,
5-(4-butyloxyphenyl)-2-[4-(2-pentyloxypropyloxy)-phenyl]pyrimidine,
5-(4-butyloxyphenyl)-2-{4-[2-(1-methylpentanoyloxy)-propyloxy]phenyl}pyrimidine,
5-(4-butyloxyphenyl)-2-}4-[2-(2-butyloxypropionyloxy)propyloxy]phenyl}pyrimidine,
2-[4-(2-hexyloxypropyloxy)phenyl]-5-(4-pentylphenyl)pyrimidine,
2-{4-[2-(3-methylhexanoyloxy)propyloxy]phenyl}-5-(4-pentylphenyl)pyrimidine,
5-(4-pentylphenyl)-2-{4-[2-(2-pentyloxypropionyloxy)propyloxy]phenyl}pyrimidine,
2-[4-(2-pentanoyloxypropyloxy)phenyl]-5-(4-pentyloxyphenyl)pyrimidine,
2-{4-[2-(2-butyloxypropionyloxy)propyloxy]phenyl}-5-(4-pentyloxyphenyl)pyrimidine,
2-[4-(2-butyryloxypropyloxy)phenyl]-5-(4-hexylphenyl)pyrimidine,
2-{4-[2-(2-propyloxypropionyloxy)propyloxy]phenyl}-5-(4-hexylphenyl)pyrimidine,
5-(4-hexyloxyphenyl)-2-[4-(2-propyloxypropyloxy)-phenyl]pyrimidine,
5-(4-hexyloxyphenyl)-2-{4-[2-(1-methylhexanoyloxy)-propyloxy]phenyl}pyrimidine,
5-(4-hexyloxyphenyl)-2-{4-[2-(2-pentyloxypropionyloxy)propyloxy]phenyl}pyrimidine,
2-[4-(2-butyloxypropyloxy)phenyl]-5-(4-heptylphenyl)pyrimidine,
5-(4-heptylphenyl)-2-{4-[2-(1-methylheptanoyloxy)-propyloxy]phenyl}pyrimidine,
5-(4-heptylphenyl)-2-{4-[2-(2-pentyloxypropionyloxy)propyloxy]phenyl}pyrimidine,
5-(4-heptyloxyphenyl)-2-[4-(2-pentanoyloxypropyloxy)phenyl]pyrimidine,
2-{4-[2-(2-butyloxypropionyloxy)propyloxy]phenyl}-5-(4-pentyloxyphenyl)pyrimidine,
2-[4-(2-hexanoyloxypropyloxy)phenyl]-5-(4-octylphenyl)pyrimidine,
2-{4-[2-(2-hexyloxypropionyloxy)propyloxy]phenyl}-5-(4-octylphenyl)pyrimidine,
5-(4-octyloxyphenyl)-2-[4-(2-pentyloxypropyloxy)-phenyl]pyrimidine,
2-{4-[2-(3-methylheptanoyloxy)propyloxy]phenyl}-5-(4-octyloxyphenyl)pyrimidine,
2-{4-[2-(2-heptyloxypropionyloxy)propyloxy]phenyl}-5-(4-octyloxyphenyl)pyrimidine,
2-[4-(2-butyloxypropyloxy)phenyl]-5-(4-nonylphenyl)pyrimidine,
5-(4-nonylphenyl)-2-[4-(2-pentanoyloxypropyloxy)phenyl]pyrimidine,
2-[4-(2-heptanoyloxypropyloxy)phenyl]-5-(4-nonylphenyl)pyrimidine,
2-{4-[2-(1-methylbutyryloxy)propyloxy]phenyl}-5-(4-nonylphenyl)pyrimidine,
2-{4-[2-(3-methylhexanoyloxy)propyloxy]phenyl}-5-(4-nonylphenyl)pyrimidine,
5-(4-nonylphenyl)-2-{4-[2-(2-propyloxypropionyloxy)propyloxy]phenyl}pyrimidine,
2-{4-[2-(2-butyloxypropionyloxy)propyloxy]phenyl}-5-(4-nonylphenyl)pyrimidine,
5-(4-decylphenyl)-2-[4-(2-hexyloxypropyloxy)phenyl]pyrimidine,
5-(4-decylphenyl)-2-{4-[2-(2-pentyloxypropionyloxy)propyloxy]phenyl}pyrimidine,
2-[4-(2-hexanoyloxypropyloxy)phenyl]-5-(4-decyloxyphenyl)pyrimidine,
2-[4-(2-hexanoyloxypropyloxy)phenyl]-5-(4-undecylphenyl)pyrimidine,
2-[4-(2-propyloxypropyloxy)phenyl]-5-(4-undecyloxyphenyl)pyrimidine,
2-{4-[2-(2-propyloxypropionyloxy)propyloxy]phenyl}-5-(4-undecyloxyphenyl)pyrimidine,
2-[4-(2-butyloxypropyloxy)phenyl]-5-(4-dodecylphenyl)pyrimidine,
2-{4-[2-(2-butyloxypropionyloxy)propyloxy]phenyl}-5-(4-dodecylphenyl)pyrimidine,
2-[4-(2-butyryloxypropyloxy)phenyl]-5-(4-dodecyloxyphenyl)pyrimidine,
2-[4-(2-pentyloxypropyloxy)phenyl]-5-(4-tridecylphenyl)pyrimidine,
2-{4-[2-(2-pentyloxypropionyloxy)propyloxy]phenyl}-5-(4-tridecylphenyl)pyrimidine,
2-[4-(2-pentanoyloxypropyloxy)phenyl]-5-(4-tridecyloxyphenyl)pyrimidine.

Compounds (Ib)

5-[4-(2-butyloxypropyloxy)phenyl]-2-(4-propylphenyl)pyrimidine,
5-[4-(2-hexanoyloxypropyloxy)phenyl]-2-(4-propylphenyl)pyrimidine,
5-{4-[2-(1-methylheptanoyloxy)propyloxy]phenyl}-2-(4-propylphenyl)pyrimidine,
2-(4-propylphenyl)-5-{4-[2-pentyloxypropionyloxy)-propyloxy]phenyl}pyrimidine,
2-(4-propyloxyphenyl)-5-[4-(2-pentanoyloxypropyloxy)phenyl]pyrimidine,
5-{4-[2-(2-butyloxypropionyloxy)propyloxy]phenyl}-2-(4-propyloxyphenyl)pyrimidine,
2-(4-butylphenyl)-5-[4-(2-butyryloxypropyloxy)-phenyl]pyrimidine,
2-(4-butylphenyl)-5-{4-[2-(2-propyloxypropionyloxy)-propyloxy]phenyl}pyrimidine,
2-(4-butylphenyl)-5-[4-(2-pentyloxypropyloxy)phenyl]pyrimidine,
2-(4-butyloxyphenyl)-5-{4-[2-(1-methylpentanoyloxy)-propyloxy]phenyl}pyrimidine,
2-(4-butyloxyphenyl)-5-{4-[2-butyloxypropionyloxy)-propyloxy]phenyl}pyrimidine,
5-[4-(2-hexyloxypropyloxy)phenyl]-2-(4-pentylphenyl)pyrimidine,
5-{4-[2-(3-methylhexanoyloxy)propyloxy]phenyl}-2-(4-pentylphenyl)pyrimidine,
2-(4-pentylphenyl)-5-{4-[2-(2-pentyloxypropionyloxy)propyloxy]phenyl}pyrimidine,
5-[4-(2-pentanoyloxypropyloxy)phenyl]-2-(4-pentyloxyphenyl)pyrimidine,
5-{4-[2-(2-butyloxypropionyloxy)propyloxy]phenyl}-2-(4-pentyloxyphenyl)pyrimidine,
5-[4-(2-butyryloxypropyloxy)phenyl]-2-(4-hexylphenyl)pyrimidine,
5-{4-[2-(2-propyloxypropionyloxy)propyloxy]phenyl}-2-(4-hexylphenyl)pyrimidine,
2-(4-hexyloxyphenyl)-5-[4-(2-propyloxypropyloxy)-phenyl]pyrimidine,
2-(4-hexyloxyphenyl)-5-{4-[2-(1-methylhexanoyloxy)-propyloxy]phenyl}pyrimidine,
2-(4-hexyloxyphenyl)-5-{4-[2-(2-pentyloxypropionyloxy)propyloxy]phenyl}pyrimidine,
5-[4-(2-butyloxypropyloxy)phenyl]-2-(4-heptylphenyl)pyrimidine,
2-(4-heptylphenyl)-5-{4-[2-(1-methylheptanoyloxy)-propyloxy]phenyl}pyrimidine,
2-(4-heptylphenyl)-5-{4-[2-(2-pentyloxypropionyloxy)-propyloxy]phenyl}pyrimidine, 2-(4-heptylphenyl)-5-[4-(2-pentanoyloxypropyloxy)-
phenyl]pyrimidine,
5-{4-[2-(2-butyloxypropionyloxy)propyloxy]phenyl}-2-
(4-pentyloxyphenyl)pyrimidine,
5-[4-(2-hexanoyloxypropyloxy)phenyl]-2-(4-octyl-
phenyl)pyrimidine,
5-{4-[2-(2-hexyloxypropionyloxy)propyloxy]phenyl}-
2-(4-octylphenyl)pyrimidine,
2-(4-octyloxyphenyl)-5-[4-(2-pentyloxypropyloxy)-
phenyl]pyrimidine,
5-{4-[2-(3-methylheptanoyloxy)propyloxy]phenyl}-2-
(4-octyloxyphenyl)pyrimidine,
5-{4-[2-(2-heptyloxypropionyloxy)propyloxy]phenyl}-
2-(4-octyloxyphenyl)pyrimidine,
5-[4-(2-butyloxypropyloxy)phenyl]-2-(4-nonylphenyl)-
pyrimidine,
5-[4-(2-heptanoyloxypropyloxy)phenyl]-2-(4-nonyl-
phenyl)pyrimidine,
5-{4-[2-(3-methylhexanoyloxy)propyloxy]phenyl}-2-(4-
nonylphenyl)pyrimidine,
2-(4-nonylphenyl)-5-{4-[2-propyloxypropionyloxy]-
phenyl}pyrimidine,
2-(4-decylphenyl)-5-{4-[2-(2-pentyloxypropionyloxy)-
propyloxy]phenyl}pyrimidine,
5-[4-(2-hexanoyloxypropyloxy)phenyl]-2-(4-decyloxy-
phenyl)pyrimidine,
5-[4-(2-hexanoyloxypropyloxy)phenyl]-2-(4-undecyl-
phenyl)pyrimidine,
5-[4-(2-hexanoyloxypropyloxy)phenyl]-2-(4-undecylox-
yphenyl)pyrimidine,
5-{4-[2-(2-propyloxypropionyloxy)propyloxy]phenyl}-
2-(4-undecyloxyphenyl)pyrimidine,
5-[4-(2-butyloxypropyloxy)phenyl]-2-(4-dodecyl-
phenyl)pyrimidine,
5-{4-[2-butyloxypropionyloxy)propyloxy]phenyl}-2-
(4-dodecylphenyl)pyrimidine,
5-[4-(2-butyryloxypropyloxy)phenyl]-2-(4-dodecyloxy-
phenyl)pyrimidine,
5-[4-(2-pentyloxypropyloxy)phenyl]-2-(4-tridecyl-
phenyl)pyrimidine,
5-{4-[2-(2-pentyloxypropionyloxy)propyloxy]phenyl}-
2-(4-tridecylphenyl)pyrimidine,
5-[4-(2-pentanoyloxypropyloxy)phenyl]-2-(4-
tridecyloxyphenyl)pyrimidine.

The merits of the present invention are as follows.
According to the present invention, any of the compounds can be used as components of ferroelectric liquid crystals. These compounds having substantially high values of spontaneous polarization are applicable to liquid crystal materials, especially display materials showing quick response.

Furthermore, when the compounds of the present invention are used as components of liquid crystal compositions, the compounds are very useful as components of ferroelectric liquid crystal materials showing preferable temperature regions of ferroelectric liquid crystals. Chiral nematic liquid crystal compositions obtained by adding the compounds of the present invention to nematic liquid crystal compositions are also wonderful as pitch controlling agents.

DESCRIPTION OF THE PREFERRED EMBODIMENTS

The following examples illustrate the present invention more specifically.

EXAMPLE 1

Production of S-5-(4-butylphenyl)
2-[4-(2-pentanoyloxypropyloxy)phenyl]pyrimidine (Ia)
wherein $R^1$ indicates $C_4H_9-$, and $R^2$ indicates
$-CO-C_4H_9$ 1st Step After 460 g of phosphorus oxychloride was added dropwise to 366 g of dimethylformamide at 0° C., 176.4 g of p-butylphenyl acetic acid was added little by little to the mixture at −10° C. The mixture was stirred at 20° C. for one hour, at 60° C. for two hours and at 80° C. for five hours.

Dimethylformamide was distilled away under vacuum, and the residue was added to a water solution saturated with magnesium perchlorate at −10° C. The obtained crystals were separated by filtration and washed with ether. A salt of 205.1 g was obtained and its melting point was 102.1°–102.5° C.

A mixture of 200 g of the salt, 135 g f p-benzyloxy benzamidine hydrochloride, 46 g of sodium methoxide and two liters of ethanol was refluxed for eight hours. Toluene was added to the mixture. The mixture was washed with alkali solution and then with water. The solvent was distilled away. The residue was recrystallized by using a mixture of ethanol and toluene, and 126 g of 2-(4-benzyloxyphenyl)-5-(4-butylphenyl)pyrimidine was obtained. This compound showed liquid crystal property and its phase transition temperatures were as follows.

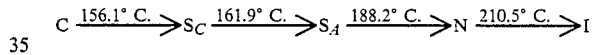

2nd Step

A mixture of 120g of 2-(4-benzyloxyphenyl)-5-(4-butylpheny)pyrimidine, 13 g of palladium active carbon, 85 g of triethylamine, four liters of ethanol and one liter of ethyl acetate was stirred under a hydrogen atmosphere. After the palladium active carbon was removed and the solvent was distilled away, the residue was recrystallized by using a mixture of n-heptane and toluene, and 86 g of 5-(4-butylphenyl)-2-(4-hydroxylphenyl)pyrimidine was obtained. This compound showed melting points of 172.5°–173.3° C.

3rd Step

To a mixture of 10 g of 60% sodium hydride, 59 g of 5-(4-butylphenyl)-2-(4-hydroxyphenyl)pyrimidine, 400 ml of tetrahydrofuran, and 800 ml of dimethylformamide, 71 g of S-2-tetrahydropyranyloxy-1-(p-toluenesulfonyloxy)propane described in Japanese patent application No. 62-132800/1987 was added. The mixture was stirred at 60° C. for four hours. Toluene was added to the mixture. After washing with an alkali solution, the mixture was washed with water and the solvent was distilled away. The residue was dissolved in 800 ml of ethanol. 80 ml of hydrochloric acid was added into the solution. The solution was stirred at about 60° C. for one hour, and cooled to room temperature. The obtained crystals were recrystallized from ethyl acetate. 48 g of S-5-(4-butylphenyl)-2-[4-(2-hydroxypropyloxy)-phenyl]pyrimidine was obtained. This compound showed liquid crystal property and its phase transition temperatures were as follows.

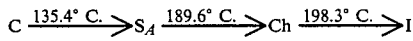

4th Step

A mixture of 5 g of S-5-(4-butylphenyl)-2-[4-(2-hydroxypropyloxy)phenyl]pyrimidine, 4.7 g of dicyclohexylcarbodiimide, 0.35 g of dimethylaminopyridine, 2 g of n-pentanoic acid and 150 ml of dichloromethane was stirred for two hours. After the obtained crystals were filtered off, the filtrate was washed with an alkali solution and then with water. The solvent was distilled away. The residue was recrystalized from ethanol. 4 g of S-5-(4-butylphenyl)-2-[4-(2-pentanoyloxypropyloxy)phenyl]pyrimidine was obtained. The compound was identified by elemental analysis, NMR-spectrum and IR-spectrum. This compound showed liquid crystal property and its phase transition temperature were as follows.

EXAMPLE 2

Production of S-5-(4-butylphenyl)-2-{4-[2-(S-2-butyloxypropionyloxy)propyloxy]phenyl}pyrimidine (Ia) wherein $R^1$ indicates $C_4H_9-$, and $R^2$ indicates

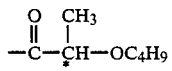

A mixture of 5 g of S-5-(4-butylphenyl)-2-[4-(2-hydroxypropyloxy)phenyl]pyrimidine, 4.7 g of N,N'-dicyclohexylcarbodiimide, 0.35 g of 4-N,N-dimethylaminopyridine, 3 g of S-2-butyloxypropanoic acid and 150 ml of dichloromethane was stirred for two hours. The obtained crystals were filtered off, and the filtrate was washed with an alkali solution, and then with water. After the solvent was distilled away, the residue was recrystallized from ethanol, and 3 g of S-5-(4-butylphenyl)-2-{4-[2-(S-2-butyloxypropionyloxy)propyloxy]phenyl}pyrimidine was obtained. The compound was identified by elemental analysis, NMR-spectrum and IR-spectrum. This compound showed liquid crystal property and its phase transition temperatures were as follows.

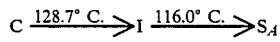

EXAMPLE 3

Production of R-5-(4-butylphenyl)-2-[4-(2-hexyloxypropyloxy)phenyl]pyrimidine (Ia) wherein $R^1$ indicates $C_4H_9-$, and $R^2$ indicates $-C_6H_{13}$ To a mixture of 5 g of R-5-(4-butylphenyl)-2-[4-(2-hydroxypropyloxy)phenyl]pyrimidine which was obtained by the same method as in Example 1, 0.6 g of 60% sodium hydride and 30 ml of tetrahydrofuran, 2.4 g of hexylbromide was added. The mixture was stirred at 60° C. for four hours. Toluene was added to the mixture. After washing with an alkali solution, the mixture was washed with water, and the solvent was distilled away. The residue was recrystallized from etha- nol. 4.8 g of R-5-(4-butylphenyl)-2-[4-(2-hexyloxypropyloxy)phenyl]pyrimidine was obtained. The compound was identified by elemental analysis, NMR-spectrum and IR-spectrum. This compound showed liquid crystal property and its phase transition temperature were as follows.

EXAMPLE 4

Production of S-5-{4-[2-(2-butyloxypropionyloxy)propyloxy]phenyl}-2-(4-nonylphenyl)pyrimidine (Ib) wherein $R^1$ indicates $C_9H_{19}-$, and $R^2$ indicates

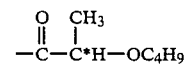

1st Step

Production of 5-(4-methoxyphenyl)-2-(4-nonylphenyl)pyrimidine

After 184 g of phosphorus oxychloride was added dropwise to 146 g of dimethylformamide at 0° C., 66 g of p-methoxyphenylacetic acid was added little by little to the mixture at $-10°$ C. The mixture was stirred at 20° C. for one hour, at 60° C. for two hours and at 80° C. for five hours. Dimethylformamide was distilled away under vacuum, and the residue was cooled and added to a water solution saturated with magnesium perchlorate. The obtained crystals were separated by filtration and washed with ether. A salt of 67 g was obtained and its melting point was 133.3°–134.4° C.

A mixture of 60 g of the salt, 48 g of p-nonyl benzamidine hydrochloride, 13.6 g of sodium methoxide and 600 ml of ethanol was refluxed for six hours. Toluene was added to the mixture. The mixture was washed with alkali solution and then with water. The solvent was distilled away. After recrystallization of the residue by using a mixture of ethanol and ethyl acetate, 60 g of 5-(4-methoxyphenyl)-2-(4-nonylphenyl)pyrimidine was obtained. This compound showed liquid crystal property and its phase transition temperatures were 88.9° C. at C—$S_A$ phase, 186.0° C. at $S_A$—N phase and 194.4° C. at N—I phase.

2nd Step

Production of 5-(4-hydroxyphenyl)-2-(4-nonylphenyl)pyrimidine

A mixture of 60 g of 5-(4-methoxyphenyl)-2-(4-nonylphenyl)pyrimidine, 240 g of hydrobromic acid and one liter of acetic acid was refluxed for 40 hours. After a large portion of acetic acid was distilled away, the residue was added to a solution of 2N sodium hydroxide. The obtained crystals were recrystallized from ethyl acetate, and 32.6 g of 5-(4-hydroxyphenyl)-2-(4-nonylphenyl)pyrimidine was obtained. This compound showed liquid crystal property and its phase transition temperatures were 98.4° C. at C—$S_A$ phase and 138.6° C. at $S_A$—I phase.

3rd Step

Production of 5-[4-(2-hydroxypropyloxy)phenyl[-2-(4-nonylphenyl)-pyrimidine

To 2.8 g of sodium hydride in 20 ml of tetrahydrofuran, 20 g of 5-(4-hydroxyphenyl)-2-(4-nonylphenyl)-pyrimidine in 100 ml of tetrahydrofuran was added slowly and 200 ml of dimethylformamide was added. The mixture was stirred for one hour.

Using the same method as described in Japanese patent application No. 61-133269, 20g of S-2-tetrahydropyranyloxy-1-(p-toluenesulfonyloxy)propane was added to the above mixture and stirred at about 65° C. for three hours. Toluene was added to the mixture. After washing with a solution of 2N sodium hydroxide, the mixture was washed with water and toluene was distilled away. The residue was dissolved in 300 ml of ethanol. 300 ml of hydrochloric acid was added into the solution and stirred at about 60° C. for two hours. A solution of 2N sodium hydroxide was added to the mixture and the mixture became basic solution. The obtained crystals were filtered and recrystallized from ethyl acetate. 11.6 g of 5-[4-(2-hydroxypropyloxy)-phenyl]-2-(4-nonylphenyl)pyrimidine was obtained. This compound showed liquid crystal property and its phase transition temperatures were 96.8° C. at C—$S_A$-phase and 211.1° C. at $S_A$-I phase.

4th Step

Production of the title compound

A mixture of 5 g of 5-[4-(2-hydroxypropyloxy)-phenyl]-2-(4-nonylphenyl)pyrimidine, 2.6 g of S-2-butyloxypropanic acid, 4 g of dicyclohexylcarbodiimide, 0.3 g of dimethylaminopyridine and 60 ml of dichloromethane was stirred for two hours. After the obtained crystals were filtered off, toluene was added to the filtrate. The mixture was washed with an alkali solution and then with water. The solvent was distilled away. 4 g of S-5-{4-[2-butyloxypropionyloxy)propyloxy]phenyl}-2-(4-nonylphenyl)pyrimidine was obtained by recrystallization from a mixed solution of ethanol and ethyl acetate. Its melting point was 98.0° C.

The following found values of elemental analysis agreed very closely with the calculated values.

| Analysis: $C_{35}H_{47}O_4N_2$ | | |
|---|---|---|
| | Found | Calculated |
| C | 74.90% | 75.10% |
| H | 8.40% | 8.46% |
| O | 11.30% | 11.43% |
| N | 5.20% | 5.01% |

EXAMPLE 5

(USE EXAMPLE 1)

Firstly, a composition was prepared by using the following liquid crystal compounds.

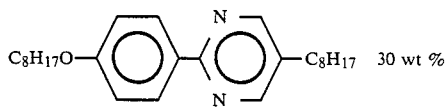 30 wt %

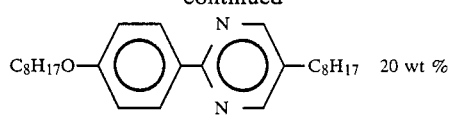 20 wt %

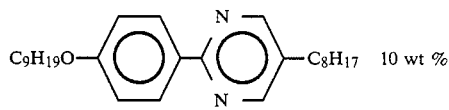 10 wt %

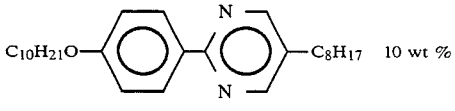 10 wt %

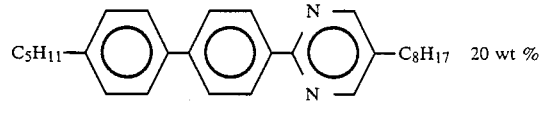 20 wt %

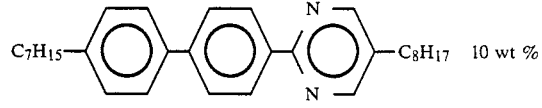 10 wt %

The phase transition temperatures of the above composition were as follows:

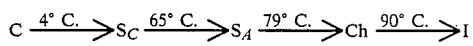

The composition was not ferroelectric.

By adding 20% by weight of the compound obtained by Example 2, namely S-5-(4-butylphenyl)-2{4-[2-(S-2-butyloxypropionyloxy)propyloxy]phenyl}pyrimidine to 80% by weight of the above composition, a chiral smectic liquid crystal composition was prepared. The phase transition temperatures were as follows.

Furthermore, the composition showed 11.5 $nC/cm^2$ of spontaneous polarization and 6.0° of tilt angle at 15° C.

This composition was injected into a cell of 2 μm thickness having transparent electrodes treated by parallel aligning treatment. The treatment was conducted by application of polyvinylalcohol as an aligning agent to the surfaces of the electrodes and rubbing the applied surfaces. The resulting element of liquid crystals was placed between a polarizer and an analyzer which intersect each other. Five volts was applied to the element. The change of transmittance of light was observed.

The response time of the element that was determined by the intensity change of transmittance light was 40 μsec. at 15° C.

According to this example, it was confirmed that the compounds of the present invention were useful ferroelectric liquid crystal materials to realize a quick response.

EXAMPLE 6

(USE EXAMPLE 2)

By adding 1% by weight of the compound of the present invention, namely S-5-(4-butylphenyl)-2-[4-(2- pentanoyloxypropyloxy)phenyl]pyrimidine obtained in Example 1 to a nematic liquid crystal composition (ZLI 1132 prepared by Merck Company), a chiral nematic liquid crystal composition was prepared. This composition was injected into a wedge-shaped cell obtained by parallel aligning treatment. The resulting cell was observed under a polarization microscope, and helical pitches were found as follows.

| Temperature °C. | 20 | 25 | 30 | 40 | 50 | 60 | 70 |
|---|---|---|---|---|---|---|---|
| Pitch length μm | 10.9 | 10.9 | 11.0 | 11.0 | 11.1 | 11.1 | 10.8 |

According to this example, it was confirmed that the compounds of the present invention were superior pitch control agents of the chiral nematic liquid crystal compositions because the temperature dependence of the pitch was very little.

EXAMPLE 7
(USE EXAMPLE 3)

A nematic liquid crystal composition containing the following compounds:

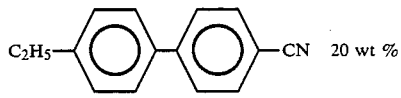 20 wt %

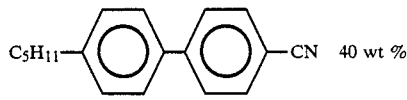 40 wt %

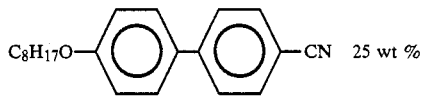 25 wt %

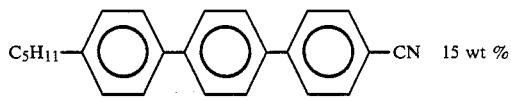 15 wt % was injected into a cell of 10 μm thick having electrodes. The cell was treated by application of polyvinyl-alcohol as an aligning agent to the surfaces of the electrodes and rubbing the applied surfaces. The resulting TN type cell was observed under a polarization microscope, and it was found that reverse twist domain was produced.

To the above nematic liquid crystal composition, 0.1 percent by weight of the compound of the present invention, namely S-5-(4-butylphenyl)-2-[4-(2-pentanoyloxypropyloxy)phenyl]pyrimidine obtained in Example 1 was added.

The TN type cell obtained by the same method as described in the above was observed under the polarization microscope. The reverse twist domain was dissolved, and a homogeneous nematic phase was observed.

What is claimed is:

1. An optically active compound represented by the formula:

wherein $R^1$ is alkyl or alkoxy having 4–12 carbon atoms, $R^2$ is alkyl, acyl or alkoxyacyl having 4–8 carbon atoms,

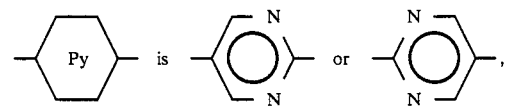

and * indicates an asymmetric carbon atom.

2. An optically active compound as claimed in claim 1, wherein $R^1$ is alkyl having 4–12 carbon atoms.

3. An optically active compound as claimed in claim 1, wherein $R^2$ is alkyl having 4–8 carbon atoms.

4. An optically active compound as claimed in claim 1, wherein $R^2$ is acyl having 4–8 carbon atoms.

5. An optically active compound as claimed in claim 1, wherein $R^2$ is alkoxyacyl having 4–8 carbon atoms.

6. An optically active compound as claimed in claim 2, wherein $R^2$ is hexyl.

7. An optically active compound as claimed in claim 2, wherein $R^2$ is $-COC_4H_9$ or

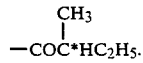

8. An optically active compound as claimed in claim 2, wherein $R^2$ is

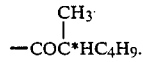

9. A liquid crystal composition comprising at least two components, at least one of which is an optically active compound as set forth in claim 2.

10. A liquid crystal composition as claimed in claim 9, exhibiting a chiral smectic phase.

11. A liquid crystal composition as claimed in claim 9, exhibiting a chiral nematic phase.